United States Patent
Sapiens

(10) Patent No.: US 11,497,395 B2
(45) Date of Patent: Nov. 15, 2022

(54) METHOD AND APPARATUS FOR MODELING AN EYE

(71) Applicant: Noam Sapiens, Newark, CA (US)

(72) Inventor: Noam Sapiens, Newark, CA (US)

(73) Assignee: EyeQue Inc., Newark, CA (US)

( * ) Notice: Subject to any disclaimer, the term of this patent is extended or adjusted under 35 U.S.C. 154(b) by 416 days.

(21) Appl. No.: 16/699,396

(22) Filed: Nov. 29, 2019

(65) Prior Publication Data

US 2020/0170500 A1    Jun. 4, 2020

Related U.S. Application Data

(60) Provisional application No. 62/773,024, filed on Nov. 29, 2018.

(51) Int. Cl.
*A61B 3/00*    (2006.01)

(52) U.S. Cl.
CPC .......... *A61B 3/0025* (2013.01); *A61B 3/0041* (2013.01)

(58) Field of Classification Search
CPC .... A61B 3/0025; A61B 3/0041; G09B 23/28; G09B 23/30
USPC ........................................................ 351/206
See application file for complete search history.

(56) References Cited

U.S. PATENT DOCUMENTS

| | | | | |
|---|---|---|---|---|
| 4,798,457 A | * | 1/1989 | Morohashi | A61B 3/0285 351/234 |
| 5,104,214 A | * | 4/1992 | Sims | A61B 3/0285 351/229 |
| 5,113,287 A | * | 5/1992 | Nakayama | G02B 15/1421 359/683 |
| 7,742,244 B2 | * | 6/2010 | Liu | A61B 3/0025 351/205 |
| 8,755,124 B2 | * | 6/2014 | Aschwanden | G02B 26/004 359/666 |
| 2012/0287398 A1 | * | 11/2012 | Baker | A61B 3/103 351/201 |

FOREIGN PATENT DOCUMENTS

DE    10341161 B3  *  2/2005  ........ G01M 11/0235

* cited by examiner

*Primary Examiner* — Mohammed A Hasan
(74) *Attorney, Agent, or Firm* — Steven A. Nielsen; www.NielsenPatents.com

(57) ABSTRACT

The invention may include a fixed lens (perhaps to simulate a cornea), a pair of Stokes lenses, an iris, deformable lens and an array detector. The implementation or construction of the disclosed embodiments follow and/or simulate the anatomy and geometry of an eye. Several optical and practical constraints were overcome by creating equivalent systems.

18 Claims, 2 Drawing Sheets

METHOD AND APPARATUS FOR MODELING AN EYE

CROSS-REFERENCE TO RELATED APPLICATIONS

This application claims the priority of and benefit of U.S. provisional patent application 62/773,024 filed on Nov. 29, 2018.

COPYRIGHT AND TRADEMARK NOTICE

This application includes material which is subject or may be subject to copyright and/or trademark protection. The copyright and trademark owner(s) has no objection to the facsimile reproduction by any of the patent disclosure, as it appears in the Patent and Trademark Office files or records, but otherwise reserves all copyright and trademark rights whatsoever.

BACKGROUND OF THE INVENTION

(1) Field of the Invention

The invention generally relates to vision simulation systems. More particularly, the invention relates to means and methods of creating and manipulating an artificial eye.

(2) Description of the Related Art

The known related art fails to anticipate or disclose the principles of the present invention.

In the related art, general methods and systems of measuring optical characteristics are known and include:

Stokes G. G., "On a mode of measuring the astigmatism of a defective eye", Mathematical and Physical paper, Cambridge University Press, 2, 172-5, 1883.

Arines J., Acosta E., "Adaptive astigmatism-correction device for eyepieces", Opt. and Vis. Sci. 88(12), 2011.

GENERAL BACKGROUND

The modeling or simulation of an eye would be useful in developing and testing at home vision testing systems.

Vision is arguably the most important of the senses. The human eye and its direct connection to the human brain is an extremely advanced optical system. Light from the environment goes through the eye optical train comprised of the cornea, the pupil, and the lens and focuses to create an image on the retina. As all optical systems, light propagation through the eye optics is subject to aberrations. The most common forms of aberrations in the eye are defocus and astigmatism. These low order aberrations are the cause of the most common refractive eye conditions myopia (nearsightedness) and hyperopia (farsightedness). Higher order aberrations are also present and can be described most conveniently by the Zernike polynomials. These usually have a lower effect on visual function. The eye, like any other organ in the human body, may suffer from various diseases and disorders, the most prominent today are: cataract, AMD, glaucoma, diabetic retinopathy, dry eye.

Ophthalmic measurements are critical for eye health and proper vision. Those ophthalmic measurements could be sectioned into objective and subjective types. Objective types measurements give a metric of a physiological, physical (e.g. mechanical or optical), biological or functional without the need for input from the measured individual (patient, subject, user or consumer). Examples of objective tests include but are not limited to OCT (optical coherent tomography used to image a 3 dimensional and cross sections of the eye), scanning laser ophthalmoscope (SLO, used for spectral imaging of the retina), fundus image (used to present an image of the retina), auto-refractor (used for refraction measurement), keratometer (used for providing a profile of the cornea), tonometer (used to measure the IOP—intra ocular pressure). Subjective measurements give a metric with relation to the individual input. That is, they provide parameters that also take into consideration the brain functions, perception and cognitive abilities of the individual. Examples of subjective tests include but are not limited to visual acuity test, contrast sensitivity test, phoropter refraction test, color vision test, visual field test, and the EyeQue PVT and Insight.

Today, both objective and subjective eye exams (measurements) are done by an ophthalmologist or an optometrist. The process usually involves the patient needing to schedule an appointment, wait for the appointment, travel to the appointment location (e.g., office or clinic), wait in line, perform multiple tests using various tools and potentially moving between different technicians and different eye doctors. The prolonged wait times both for the appointment as well as in line at the appointment location, along with the hassle of performing the tests with different professionals and the duration of those tests might seem daunting to many patients. Furthermore, the shear effort associated with the process and even the requirement of remembering to start the process to begin with might deter patients from going through with a traditional examination.

Moreover, currently about 2.5 billion people do not have access to eye and vision care at all. The cost of eye exams could be considered quite significant especially in some places in the world. This poses a hindrance to the availability of eye care in third world countries for example. The cost, time consumption and perceived hassle also makes it at times prohibitive to have repeated eye exams, especially at the desired frequency. Those might be necessary in special cases (for example after refractive surgery or cataract surgery where repeated measurements should be performed to track the progress of the patient's status over time and the success of the surgery. Additionally, even under normal circumstances, measurements at a doctor's office only represent a single point in time. The situation under which the measurements were made might not be optimal or do not fully represent the patient's characteristics. The patient might have been tired, stressed or agitated (a doctor's visit might be quite stressful in and of itself but could also being run from test to test and being posed with questions and options elevate the patient's level of stress) or was just in a bad mood. Even the state of mind of the doctor themselves might influence the way the measurement is performed. Beyond all that, the time of day and other environmental conditions (whether direct e.g. lighting conditions or indirect e.g. temperature) could also affect the measurement and provide incomplete or false information.

The availability of information (including specifically medical information) on the Internet, the increased awareness of people for preventive medicine, and the emergence of tele-medicine leads to many taking control of their own health. Devices for screening, monitoring and tracking medical conditions are quite pervasive in today's world, for example blood pressure measurement devices, and blood sugar monitors. The technological advancements allow for people to be more independent in diagnosis, prevention and tracking of various health conditions. Furthermore, many prefer to perform these activities in the comfort of their homes without the need for appointments or other time-consuming activities. In case of an anomaly, they would call or email their physicians to consult for the appropriate course of action.

The advancement of technologies effectively makes computers with screens and cameras ubiquitous in the form of laptops, tablets and smartphones. Therefore, enabling many people to have a device already capable of computing displaying and recording information.

All this brings the need for a series of devices that will enable users to perform ophthalmic measurements at home, by themselves, in a timely and cost-effective manner. It should be clear that the quality of these measurements and their accuracy and precision should meet or exceed the standards of today's measurement methods.

This vision could be further enhanced by use of cloud-based data and analytics that enables complete access to the entire history of a patient exams, tests and measurements. Moreover, the use of artificial intelligence (AI) will enable diagnosis based on machine learning and big data. This could be done by means of data mining, neural network decision making and pattern detection and recognition, as some examples of the AI capabilities.

To summarize, the vision for eye care in the not so far future will look like:

A complete solution for eye and vision care for consumers and doctors.

Remote, self-administered battery of tests for both disease and functional measurements are enabled by technology and devices AI is used for analysis, tracking and reporting. Enhanced by big data correlations and insights In simple terms, as an example: A person sits on their couch at the comfort of their home, uses a device to do various measurements, that data is uploaded to an AI for analysis. The AI will let the person know the results and notify the doctor. The AI will initiate alerts for the person and doctor in necessary cases. The person will not need to get up unless a serious issue occurs (i.e. surgery). All other issues will be dealt with remotely (e.g. email/phone/video conference with the doctor, order glasses and have them delivered to the home, direct delivery of doctor prescribed medications).

Despite the apparent approach of "direct to consumer", the methodologies could easily be implemented for a more enterprise like model. One example of such implementation will have a hierarchical structure in which an entity such as a hospital, association, or a medical insurance company provides the ability for the doctors to provide their patients with such devices and capabilities. The devices are all connected through the user accounts to the cloud and the measurements are streamed directly into the users' accounts (and potentially their medical records). Those accounts could be attached to one or more doctors and can also be transferred and shared.

BRIEF SUMMARY OF THE INVENTION

The present invention overcomes shortfalls in the related art by presenting an unobvious and unique combination and configuration of methods and components to create an apparatus that may be used to calibrate systems used for home eye exams. Other uses, utility and functions of the disclosed embodiments include:

A validation system to test and confirm refraction measurements, such as the at home refractions measurements systems discussed above;

An educational tool to teach eye function and the utility of at home optical measuring systems;

An educational tool to demonstrate various ophthalmic challenges that may be of relevance to a consumer;

A marketing tool for various eye testing systems and various forms of eye correction, such as progressive lenses in eyeglasses;

An artificial eye proxy;

For the visually challenged, an artificial eye system used in conjunction with a VR/AR type display system, wherein the magnification and/or other variables could be adjusted to comport with the particular visual challenges of the user.

These and other objects and advantages will be made apparent when considering the following detailed specification when taken in conjunction with the drawings.

SHORTFALLS IN THE RELATED ART

Currently, eye function is either simulated using computer software or calculated by use of prior measurements and research. The methods of the prior art lack the realism and immediate results of an experimental model. Moreover, the systems and methods of the prior art fail to provide a physical system for real time testing of optical systems and/or eye exam systems. The disclosed embodiments overcome the prior art by, inter alia, providing for actual, real-life implementation, measurement and validation of various tools in an empirical manner that do not rely solely upon numerical simulations.

REFERENCE NUMBERS

Figure 1:
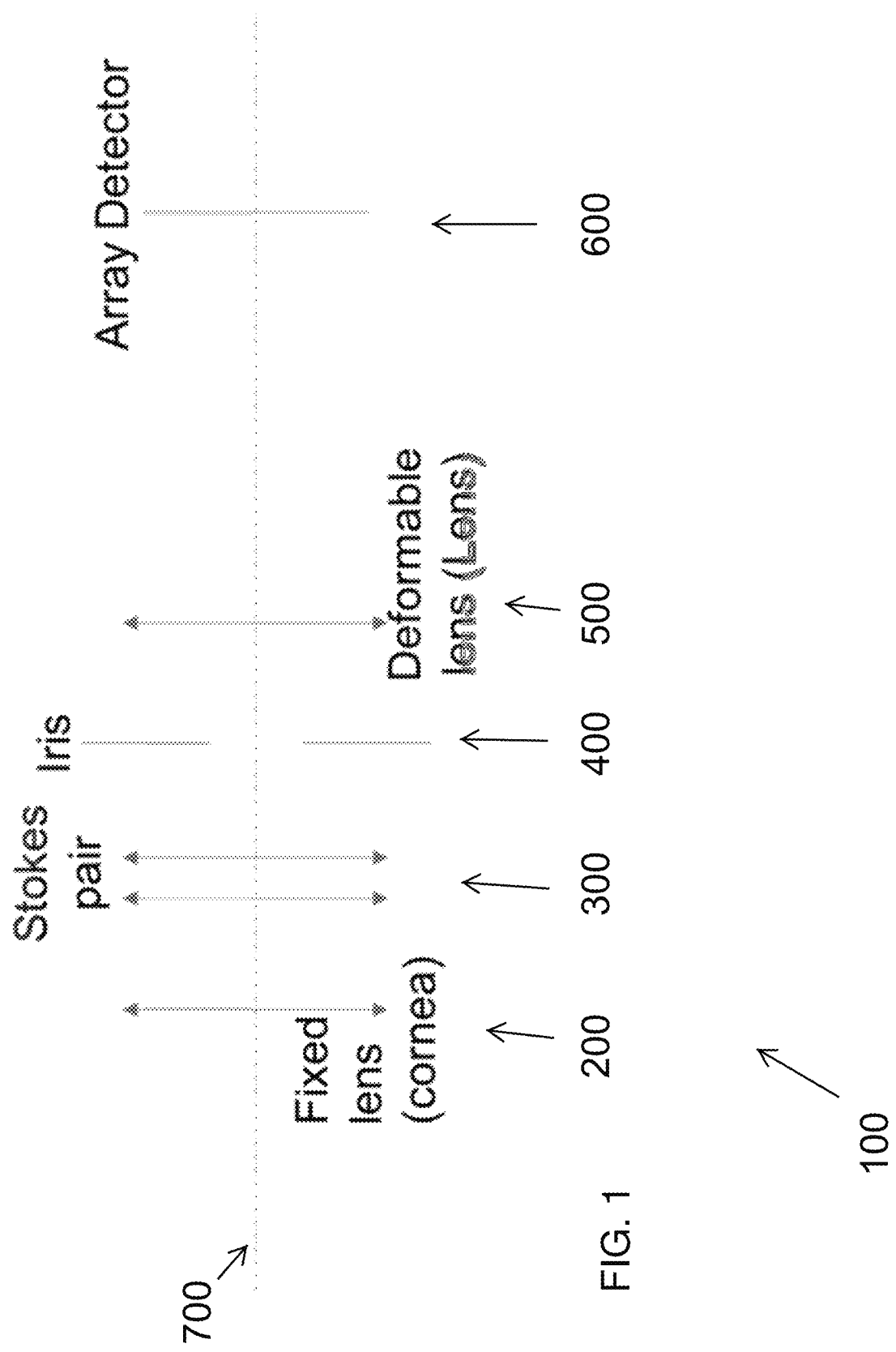
FIG. 1 depicts a construction of a disclosed embodiment

100 a disclosed system in general
200 fixed lens, such as a cornea
300 Stokes pair of lenses
400 Iris type of lens
500 Deformable lens
600 array detector
700 line of sight

DETAILED DESCRIPTION OF EMBODIMENTS OF THE INVENTION

The following detailed description is directed to certain specific embodiments of the invention. However, the invention can be embodied in a multitude of different ways as defined and covered by the claims and their equivalents. In this description, reference is made to the drawings wherein like parts are designated with like numerals throughout.

Unless otherwise noted in this specification or in the claims, all of the terms used in the specification and the claims will have the meanings normally ascribed to these terms by workers in the art.

Unless the context clearly requires otherwise, throughout the description and the claims, the words "comprise," "comprising" and the like are to be construed in an inclusive sense as opposed to an exclusive or exhaustive sense; that is to say, in a sense of "including, but not limited to." Words using the singular or plural number also include the plural or singular number, respectively. Additionally, the words "herein," "above," "below," and words of similar import, when used in this application, shall refer to this application as a whole and not to any particular portions of this application.

The above detailed description of embodiments of the invention is not intended to be exhaustive or to limit the invention to the precise form disclosed above. While specific embodiments of, and examples for, the invention are described above for illustrative purposes, various equivalent modifications are possible within the scope of the invention, as those skilled in the relevant art will recognize. For example, while steps are presented in a given order, alternative embodiments may perform routines having steps in a different order. The teachings of the invention provided herein can be applied to other systems, not only the systems described herein. The various embodiments described herein can be combined to provide further embodiments. These and other changes can be made to the invention in light of the detailed description.

Any and all the above references and U.S. patents and applications are incorporated herein by reference. Aspects of the invention can be modified, if necessary, to employ the systems, functions and concepts of the various patents and applications described above to provide yet further embodiments of the invention.

Referring to FIG. 1, a disclosed system 100 may include a fixed lens 200 (perhaps to simulate a cornea), a pair of Stokes lenses 300, an iris 400, deformable lens 500 and an array detector 600. The implementation or construction of the disclosed embodiments follow and/or simulate the anatomy and geometry of an eye. Several optical and practical constraints were overcome by creating equivalent systems as disclosed herein.

Figure 2:
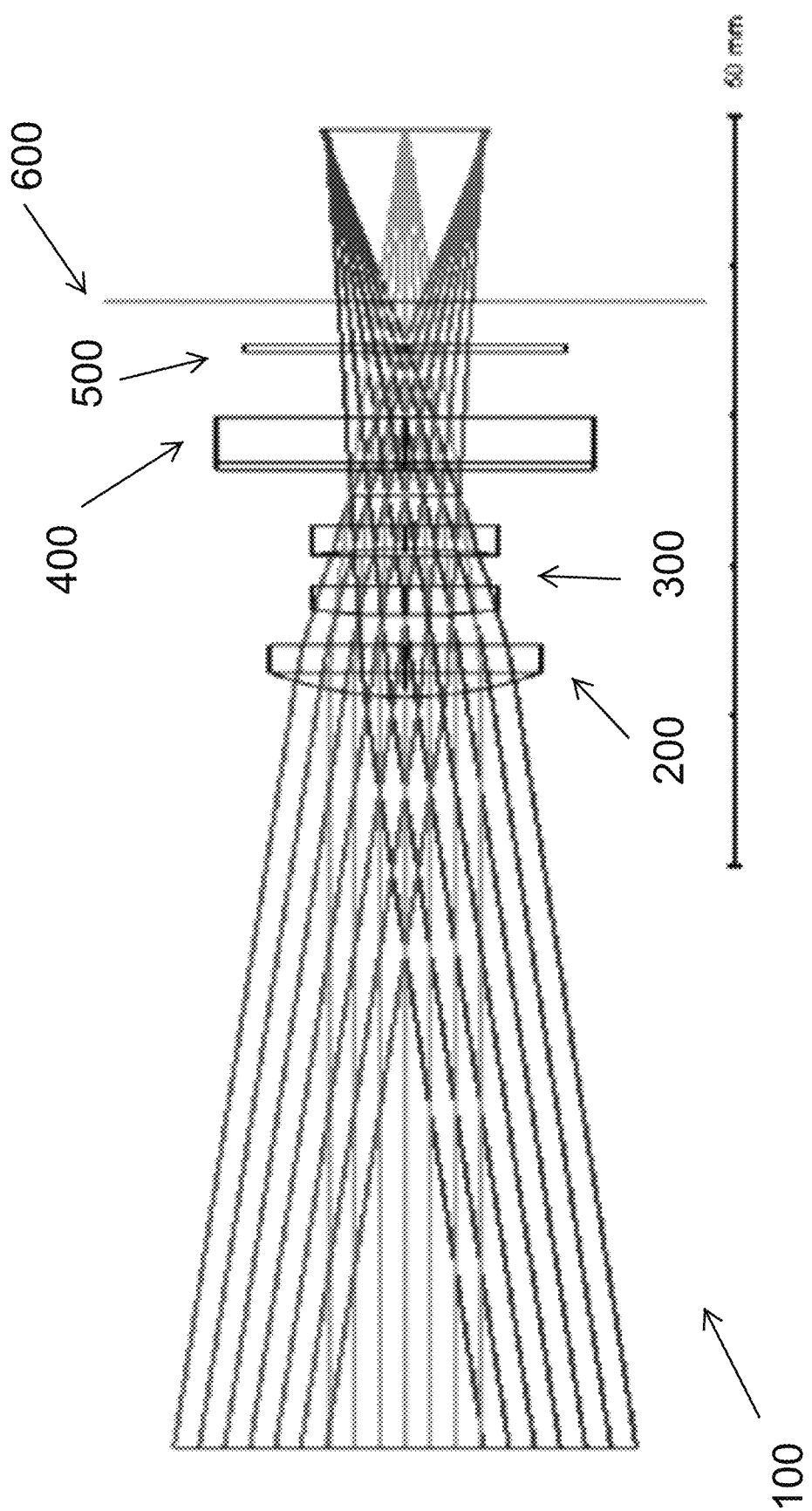
FIG. 2 depicts ray tracing of a disclosed embodiment

Referring to FIG. 2 the optical path and optical considerations of the disclosed embodiments are depicted in the form of ray tracing lines and lens representations.

Referring to FIGS. 1 and 2, a disclosed embodiment may be described wherein light, propagating from the left in figure enters the eye models through a single lens. The lens could be, without limitation a plano-convex lens, a meniscus lens, a best form lens, or achromatic lens. The lens could be made of glass or plastic, with or without coatings.

The light then continues to go through a Stokes lens pair 300, two lenses numbered collectively as 300. These two lenses are cylindrical lenses that could be rotated with respect to each other. This component introduces an astigmatism term to the eye without affecting spherical performance. The two lenses could be of the same power or have different power, for example opposite power. In the case of two opposite power lenses with power ±D, the total astigmatic power from the pair is between −2D and 2D depending on the angles between the lenses according to the following formula:

$$C = 2D \sin(\alpha)$$

Where C is the cylinder power and a is the angle between the two lenses. Rotation of both lenses together defines the axis of the cylinder.

This implementation is quite straightforward in the definition of the astigmatic power of the eye model as it is the only aspheric component in the design. In an alternative embodiment, the Stokes pair and front lens (both together mimic the cornea) could be replaced by a liquid lens that can be controlled by pulling on a membrane containing the fluid in a defined amount and direction. This implementation might closely mimic the biological eye function in terms of astigmatism. Nevertheless, it is much more complicated to fabricate.

The light in FIG. 2 then moves from the Stokes pair through a changeable iris (representing the pupil) to a deformable lens. This lens could be controlled to change its focal length by changing its shape. In one embodiment, this is a liquid lens controlled electrically by changing the pressure on a reservoir of liquid, in another this liquid lens is controlled by electro-static deformation of the membrane containing the liquid. An altogether alternative embodiment includes a pair of spherical lenses of focal lengths f1 and f2, move one in relation to the other in the optical axis direction such that the distance between them, d, changes. This will cause the effective focal length f of the pair to change based on the following formula (approximately):

$$\frac{1}{f} = \frac{1}{f_1} + \frac{1}{f_2} - \frac{d}{f_1 f_2}$$

The light from the lens will then travel to an array detector (camera). FIG. 2 presents a consideration for the determination of the size of the array. In one embodiment it could be chosen to represent the field of view (FoV) of the human macula of approximately 18°. Furthermore, the array could be chosen to detect color and provide color vision. The array's resolution could be chosen for example to be similar to that of the human macula being about 4 MP or more. The array could be a CCD or CMOS camera for example. The array could be presented as a curved array to better represent the biological eye. Furthermore, a curved array will improve the optical performance, especially with large arrays and at high FoV angles. Alternatively, the front lens (cornea lens) could be replaced with an aspheric lens to correct for the aberrations and distortion.

The design of the invention could be implemented in a way that could be scaled. Scaling may be accomplished by proportionally increasing the parameters (distances, focal lengths, diameters etc.) in the design. For example, the size of the eye could be increased by a factor, maintaining the same factor for the optical system focal length, camera sensor size and element diameters will create an embodiment of the invention with similar or identical functionality, as can be measured by functional refraction ranges and FoV, as main examples of performance metrics.

The following are aspects of the invention that pertain to specific embodiments and examples:

The entire invention could be manual, such that changes in the performance of the eye model are done by hand. Alternatively, and preferably, the invention will utilize automatic features.

The Stokes lenses could be mounted on rotation stages. These maybe based on stepper motors, servo motors, PCB motors, for example.

The iris could be made of metal or plastic for example. It could be based on a leaf design or other design that controls the amount of obscuration.

The camera could be further mounted on a translation (linear) stage allowing for changing the distance between the deformable lens (representing the eye lens) and the camera (representing the retina). This allows for experimental simulation of aging, myopia and hyperopia.

The entirety of the components in the eye model could be connected to a processing unit, e.g. a computer. The processing unit can control the model as well as receive the images from the array detector.

Various real conditions can be easily introduced in the system from a refraction standpoint, for example: myopia, hyperopia, presbyopia, accommodation.

Furthermore, some eye conditions and diseases could be simulated using the processing unit, such as: cataract, AMD, color blindness.

For presentation purposes the eye model could be placed in front of a visual acuity chart and a display could be connected to the processing unit to present what an eye with specific conditions would see.

The eye model could be used to show the effectiveness of glasses by simulating the condition and placing eyeglasses in front of the model to show the improvement on the display.

Two of the eyes could be built and placed together to allow for binocular vision and thus three-dimensional vision. That could be represented using a 3D screen/projector.

Disclosed systems may be mounted upon a moveable platform and/or upon a gimbal or gimbal type device. A disclosed system upon a moveable and/or rotatable platform may allow for the simulation of progressive lens mission. The deformable lens may in linked or otherwise influenced by the system motion to account for close and/or far vision. Furthermore, such mounted system could be created in a binocular form to simulate 3D vision and include vergence and depth perception.

What is claimed is:

1. An optical system to simulate an eye, the system comprising:
   a) a fixed lens to simulate a cornea;
   b) a Stokes pair of lenses;
   c) an iris;
   d) a deformable lens;
   e) an array detector; and
   f) the system in electronic communication with a computer system wherein the computer system controls the system to create refraction error, the refraction error being both spherical and cylindrical.

2. The system of claim 1 wherein the fixed lens is selected from the group comprising: a plano-convex lens, a meniscus lens, a best form lens and achromatic lens.

3. The system of claim 1 wherein the Stokes pair of lenses introduce astigmatism to the optical system without affecting spherical performance.

4. The system of claim 1 wherein the Stokes pair of lenses are cylindrical lenses that may be rotated with respect to one another.

5. The system of claim 1 wherein the Stokes pair of lenses are of the same power.

6. The system of claim 1 wherein the Stokes pair of lenses are of opposite power.

7. The system of claim 1 wherein the Stokes pair of lenses are opposite in power, the total astigmatic power is between −2D and 2D depending on the angles between the two Stoke lenses to comport with the formula:

$$C = 2D \sin(\alpha)$$

wherein C is the cylinder power and a is the angle between the Stokes pair of lenses and wherein rotation of the Stokes pair of lenses together defines an axis of the cylinder.

8. The system of claim 1 wherein the deformable lens is a liquid lens, the liquid lens capable of being controlled by manipulating a membrane, the membrane containing fluid.

9. The system of claim 8 wherein the liquid lens is controlled by filling the membrane with fluid of a predefined amount.

10. The system of claim 8 wherein the liquid lens is controlled by electro-static deformation of a membrane of the deformable lens with the membrane containing a liquid.

11. The system of claim 1 wherein the deformable lens comprises a pair of spherical lenses having focal lengths f1 and f2, wherein the pair of spherical lenses move in relation to the other in an optical axis direction such that the distance, d, between the pair of spherical lenses changes.

12. The system of claim 11 wherein the focal length, f, of the pair of spherical lenses changes to comport with:

$$\frac{1}{f} = \frac{1}{f_1} + \frac{1}{f_2} - \frac{d}{f_1 f_2}.$$

13. The system of claim 1 wherein the array detector is replaced by a CCD or CMOS color camera.

14. The system of claim 1 wherein the computer system controls the system to simulate eye and vision conditions.

15. The system of claim 1 wherein the computer system controls the iris to simulate pupil response and effect on an image.

16. The system of claim 1 further comprising a second system, the second system comprising the components of the first system; the first and second systems comprising a binocular viewer, the binocular viewer providing three dimensional output and depth perception.

17. An optical system to simulate an eye, the system comprising:
   a) a fixed lens to simulate a cornea;
   b) a Stokes pair of lenses;
   c) an iris;
   d) a deformable lens;
   e) an array detector;
   f) the optical system in electronic communication with a computer system, wherein the computer system controls the system to simulate eye and vision conditions; and
   g) wherein the simulated eye and vision conditions comprise: cataract, macular degeneration, myopia, hyperopia and accommodation.

18. An optical system to simulate an eye, the system comprising:
   a) a fixed lens to simulate a cornea;
   b) a Stokes pair of lenses;
   c) an iris;
   d) a deformable lens;
   e) an array detector;
   f) the system mounted upon a gimbal to enable the system to move to simulate progressive lens vision; and
   g) wherein the shape of the deformable lens changes in reaction to movement of the system such that the deformable lens comports to close and far vision.

* * * * *